United States Patent
Murray, III

(12) United States Patent Murray, III
(10) Patent No.: US 7,105,014 B2
(45) Date of Patent: Sep. 12, 2006

(54) STENT DELIVERY AND RETENTION APPARATUS

(75) Inventor: Robert J. Murray, III, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 664 days.

(21) Appl. No.: 10/302,472

(22) Filed: Nov. 22, 2002

(65) Prior Publication Data

US 2004/0102791 A1 May 27, 2004

(51) Int. Cl.
*A61F 11/00* (2006.01)
(52) U.S. Cl. .............. 623/1.11; 606/194; 606/198; 606/191; 604/103.04; 604/103.07
(58) Field of Classification Search ............... 623/1.11, 623/901; 606/194, 198, 191, 108; 604/103.07, 604/194, 103.04
See application file for complete search history.

(56) References Cited

U.S. PATENT DOCUMENTS

| 5,836,965 | A  | * | 11/1998 | Jendersee et al. | 623/1.11 |
| 8,395,008 |    |   | 5/2002  | Ellis et al.     |          |
| 6,663,660 | B1 | * | 12/2003 | Dusbabek et al.  | 623/1.11 |
| 6,837,897 | B1 | * | 1/2005  | Holman et al.    | 606/194  |
| 6,948,223 | B1 | * | 9/2005  | Shortt           | 29/272   |

* cited by examiner

*Primary Examiner*—Michael J. Hayes
*Assistant Examiner*—M. Thomas Andersen

(57) ABSTRACT

A stent delivery system comprises an inner member and an expandable balloon mounted in a collapsed state on the inner member, the expandable balloon having a first and a second end. A compressible stent having a first diameter is mounted in a compressed state around the expandable balloon between the first and second ends of the balloon. At least a first retainer pillow is formed in the expandable balloon at its first end and has an outer diameter which is at least substantially equal to the diameter of the compressed stent. A first pillow support member is mounted on the inner member and supports the first retainer pillow to maintain the pillow's outer diameter.

5 Claims, 3 Drawing Sheets

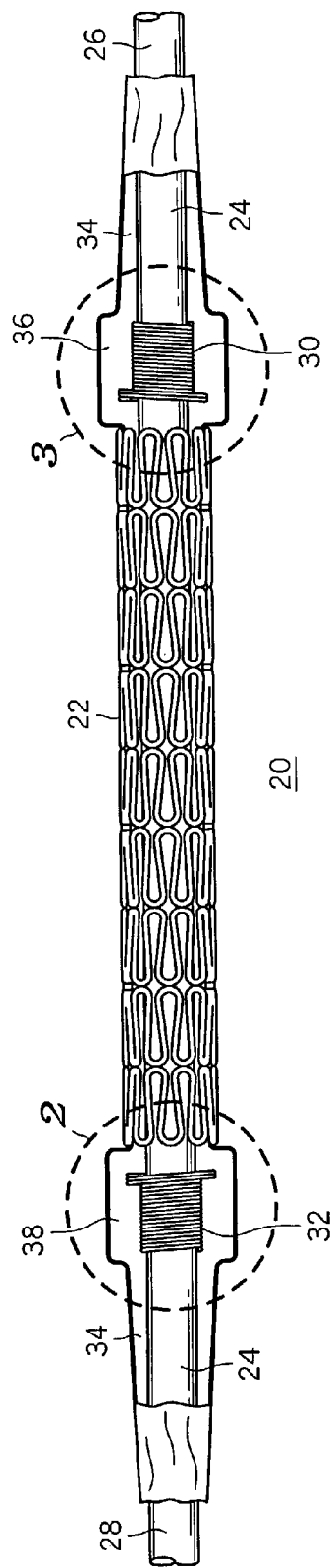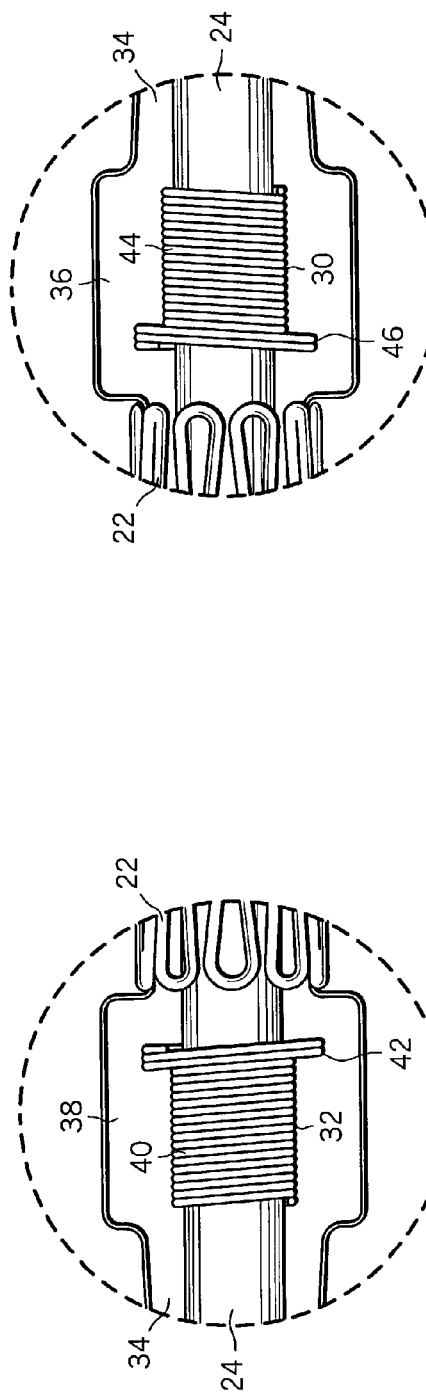

STENT DELIVERY AND RETENTION APPARATUS

FIELD OF THE INVENTION

This invention relates generally to an intravascular stent deployment apparatus, and more particularly to a stent delivery apparatus including marker bands which support distal and proximal pillows to provide mechanical stent retention.

BACKGROUND OF THE INVENTION

In a typical percutaneous transluminal coronary angioplasty (PTCA) procedure, a guiding catheter is percutaneously introduced into the cardiovascular system of a patient. The guide catheter is advanced through a vessel until the distal end thereof is at desired location in the vasculature. A guide wire and a dilatation catheter having a balloon on the distal end thereof are introduced into the guiding catheter with the guidewire sliding through the dilatation catheter. The guide wire is first advanced out of the guiding catheter into the patient's coronary vasculature, and the dilatation catheter is advanced over the previously advanced guide wire until the dilatation balloon is properly positioned across the lesion. Once in position, the flexible, expandable, preformed balloon is inflated to a predetermined size with a liquid or gas at relatively high pressures (e.g. about ten to twelve atmospheres) to radially compress the arthrosclerotic plaque in the lesion against the inside of the artery wall and thereby dilate the lumen of the artery. The balloon is then deflated to a small profile so that the dilatation catheter may be withdrawn from the patient's vasculature and blood flow resumed through the dilated artery.

In angioplasty procedures of the kind described above, there may occur a restenosis of the artery; i.e., a re-narrowing of the treated coronary artery which is related to the development of neo-intinmal hyperplasia that occurs within the artery after it has been treated as described above. In a sense, restenosis is scar tissue that forms in response to mechanical intervention within a vascular structure. To prevent restenosis and strengthen the area, an intravascular prosthesis generally referred to as a stent can be implanted for maintaining vascular patency inside the artery at the lesion. The stent is then expanded to a larger diameter for placement or implantation in the vasculature. This is often accomplished by the balloon portion of the catheter. The stent effectively overcomes the natural tendency of the vessel walls of some patients to close back down, thereby maintaining a normal flow of blood through the vessel that would not be possible if the stent was not in place.

A known expandable stent which is delivered on a balloon catheter may be considered to be a stainless steel cylinder having a number of openings in its circumference resulting in a scaffolding when expanded. The stainless steel cylinder is compressed onto the outside of a non-expanded balloon catheter which includes stent retainer rings at each end of the stent to help maintain the stent on the balloon. Unfortunately, the limited amount of securment between the stent and the balloon is not always adequate to insure that the stent will properly stay in place while advancing the stent to and through a target lesion. Additionally, the outer surface of the delivery device is uneven because the stent generally extends outwardly beyond the balloon. Thus, the stent may contact a narrow vessel wall and be displaced while the catheter negotiates a narrow vessel. Furthermore, during a coronary intervention, the physician may have difficulty crossing the target lesion. In such cases, it may be necessary to pull the stent delivery system back into the guide catheter. Such procedures can be risky because the stent may become caught on the edge of the guide catheter.

For example, the guide catheter is generally inserted through the abdominal aorta to a point just beyond the ostium, the location from which the right coronary artery and the left main artery diverge. Blockages or lesions are present in smaller coronary vessels, and medical practitioners may sometimes predilatate the target area as, for example, by balloon angioplasty. Sometimes, however, predilatation is not performed, and doctors proceed directly to a primary stenting procedure. In such cases, there are occasions when the balloon/stent catheter cannot be properly positioned within the target area due to the constriction of the vessel and must be retracted back into the guide catheter. Even when predilatation is performed, vascular spasms and/or a reclosure of the vessel may occur rendering it difficult to properly align the balloon/stent likewise requiring retraction into the guide catheter. It is during the retraction process that the stent can catch or impact the edge of the guide catheter causing it to be dislocated or otherwise damaged.

To migrate this problem, balloon pillow have been utilized to provide a smooth transition of the balloon/stent assembly back into the guide catheter. Such balloons may be produced through a process of heating and cooling in, for example, Teflon sheaths which are stacked in a way to produce a step in the collapsed balloon surface. One such system is shown and described in U.S. Pat. No. 5,836,965 issued Nov. 17, 1998 and entitled "Stent Delivery and Deployment Method." In this apparatus, pillows formed in the balloon at opposite ends of the stent assist and secure the stent to the balloon and create a smooth transition between the stent area and the distal and proximal surface of the delivery device. The balloon may be tapered or non-tapered. Additionally, conventional retainers may be attached over the balloon or placed within the balloons. Unfortunately, the balloon material is generally very pliable, and it has been found that when using such devices, the pillows may collapse under the pressure of insertion and/or retraction thus exposing the edge of the stent to the potential impact on the edge of the guide catheter.

It should therefore be appreciated that it would be desirable to provide a low profile stent delivery apparatus which may be configured to have a generally smooth outer surface so as to avoid collisions between the stent and other obstructions such as the edge of the guide catheter.

SUMMARY OF THE INVENTION

According to an aspect of the invention, there is a provided a stent delivery system comprising an inner member and an expandable balloon mounted in a collapsed state on the inner member, the expandable balloon having the first end and a second end. A compressible stent is mounted in a compressed state of a first diameter around the expandable balloon between the first and second ends. At least a first retainer pillow is formed in the expandable balloon at the first end and has an outer diameter which is at least substantially equal to the diameter of the stent. A first pillow support member is mounted on the inner member and supports the first retainer pillow to maintain its outer diameter.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed descriptions. The present invention will hereinafter be described in conjunction with the appended drawings, wherein like reference numerals denote like elements, and;

FIG. 1 is a longitudinal cross sectional view of a stent and balloon assembly utilizing marker band support devices in accordance with the present invention;

FIG. 2 is an enlarged view of the proximal marker band and pillow support assembly shown in FIG. 1;

FIG. 3 is an enlarged view of the distal marker band and pillow support assembly shown in FIG. 1;

DETAILED DESCRIPTION OF THE EXEMPLARY EMBODIMENT

Figure 4:
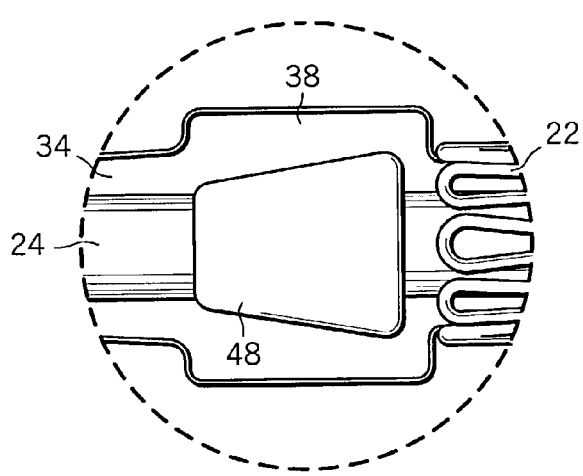
FIG. 4 is an enlarged view of a marker band and pillow support assembly in accordance with a farther embodiment of the present invention.

The following description is exemplary in nature and is not intended to limit the scope, applicability, or configuration of the invention in any way. Rather, the following description provides a convenient illustration for implementing an exemplary embodiment of the invention. Various changes to the described embodiments may be made in the function and arrangement of the elements described herein without departing from the scope of the invention.

FIG. 1 is a longitudinal, cross-sectional view of a balloon/stent assembly embodying the principles of the present invention. The balloon/stent assembly shown generally at 20 comprises a stent 22, an inner member or wire lumen 24 having a distal end 26 and a proximal end 28, and distal and proximal radiopaque marker bands 30 and 32 respectively which are positioned on inner member or wire lumen 24 substantially adjacent to distal and proximal ends of stent 22. Stent 22 may be of any form or configuration suitable for the intended purpose, and may comprise one or more stent segments depending on the size and configuration of the vessel to be treated. It will be recognized by those skilled in the art that inner member or guide lumen 24 is configured for the insertion of a conventional guide wire (not shown) which will enable the stent/balloon assembly to be guided and positioned at a target location in the vessel to be treated.

Any conventional or modified balloon catheter device may be used such as a PTCA balloon catheter. An expandable balloon portion 34 is mounted on inner member 24 in a compressed or collapsed state beneath stent 22 and extending beyond the proximal and distal ends of stent 22. Balloon 34 is generally made of a pliable material such as polyethylene, polyethylene terathalate, PEBAX (polyamide block copolymers and polyester block copolymers), polyvinyl chloride, polyolefin, nylon or the like. The length and the diameter of the balloon may be selected to accommodate the particular configuration of the stent to be deployed. Stent 22 may be constructed of any implantable material having good mechanical strength, such as stainless steel, titanium, tantalum, super-elastic nickel-titanium alloys, or high-strength thermoplastic polymers. The outside of the stent may be selectively plated with platinum or other implantable radiopaque substance to provide visibility during fluoroscopy. The cross sectional shape and the finished stent 22 maybe circular, ellipsoidal, rectangular, hexagonal, square, or any other desired shape, although a circular or ellipsoidal cross section is preferable. The length and width of stent 22 is generally determined to a large degree by the size of the vessel into which the stent will be deployed. It must be of sufficient length to maintain its axial orientation without shifting under the hydraulics of blood flow, long enough to extend across a significant portion of the target area, and at the same time not be unnecessarily long so as to result in the introduction of an unnecessarily large amount of material into the vessel.

After stent selection, the stent 22 is compressed upon the outside of balloon 34. An inner sheath (not shown) is placed over each end of balloon 34 and an exterior sheath (also not shown), is placed over the ends of the interior sheath so as to cover stent 22 and overlap with the interior sheaths. The assembly is then pressurized by introducing air or an inert gas such as nitrogen through the lumen 24 into the interior of balloon 34 so as to expand the balloon within the sheaths. The assembly is then exposed to an elevated temperature while maintaining pressurization of the balloon. The pressure may be, for example, approximately 70 psi and the temperature approximately 150 degrees Fahrenheit. Following heating, the balloon/stent assembly is allowed to cool within the sheaths, and this cooling sets the shape of balloon 34. The sheaths may then be removed. Depending on the relative positioning of the inner and outer sheaths and stent 22 during the pressurizing, heating, and cooling process, there will be formed distal and proximal retainers or pillows 36 and 38 respectively which are intended to secure stent 22 in position around balloon 34 and provide a smooth transition between the balloon/stent portion of the delivery device and the distal and proximal ends of the delivery device.

Marker bands which may be viewed through fluoroscopy assist in positioning the assembly. When the assembly is properly located across a lesion, the balloon may be inflated in a conventional manner. This results in the general uniform, symmetrical expansion of the stent and balloon. The amount of inflation and thus the amount of expansion of the stent may be varied as dictated by the lesion itself. The process by which retainers or pillows 36 and 38 are formed is described in detail in U.S. Pat. No. 5,836,965 entitled "Stent Delivery and Deployment Method" issued Nov. 17, 1998, the teachings of which are hereby incorporated by reference.

As stated previously, there are occasions when the balloon/stent catheter cannot be properly positioned within the target area due to the constriction of the vessel and therefore must be retracted back into the guide catheter. During this retraction process, the edge of the stent might catch or impact the edge of the guide catheter causing it to be dislocated or otherwise damaged. Pillow 38 has an outer diameter which is equal to or greater than the outer diameter of stent 22 and therefore assists in providing a smooth transition between balloon 34 and stent 22 as it is retracted. Furthermore, the lesion may be heavily calcified requiring a higher insertion pressure. In this case, balloon 36 having an outer diameter which is at least equal to the outer diameter of stent 22 likewise represents an effort to provide a smooth transition between balloon 34 and stent 22 at the distal edge of stent 22. Unfortunately, as already mentioned, the balloon material is generally very pliable and as a result, pillows 38 and/or 34 may collapse thereby exposing the proximal edge of stent 22 during retraction and/or the distal edge of stent 22 during insertion.

To prevent collapse of pillows 36 and 38, marker bands 32 and 30 are provided with regions of higher diameter for supporting pillows 38 and 36 as is shown in more detail in FIG. 2 and FIG. 3 respectively. Thus, the marker bands not only assist in the proper positioning of the stent within the target lesion, but also support the retainer pillows during the insertion and/or retraction process.

Referring to FIG. 2, there is shown a marker band or pillow support member 32 which includes a first region 40 having an inner diameter sufficiently large to be frictionally or adhesively coupled on the inner member or wire lumen 24. The distal end of pillow support member 32 includes a section 42 which is fixedly coupled to section 40 and has an outer diameter which approximates the outer diameter of stent 22 so as to maintain the pillow diameter at least equal to or greater than the outer diameter of stent 22. That is, section 42 supports pillow 38 in such a manner as to maintain its outer diameter equal to or greater than the outer diameter of stent 22 so as to prevent the collapse of pillow 38 and thereby provide a smooth transition should it be necessary to retract the stent/balloon assembly be back into the guide catheter.

In a similar manner, marker band or pillow support member 30, shown in FIG. 3, includes a first or distal section 44 having an outer diameter which is just sufficient to be mounted on inner member or wire lumen 24 and to be retained thereon. Support member 30 includes a proximal section 46 which is fixedly coupled to or formed integrally with section 44 and has an outer diameter which is larger than that of section 44 so as to maintain the outer diameter of pillow 36 at least equal to the outer diameter of stent 22. In this manner, pillow 36 is prevented from collapsing should additional pressure be required to insert the stent/balloon assembly into a target lesion which is highly calcified.

In the embodiment shown in FIGS. 1, 2, and 3, pillow support members 30 and 32 are coiled, spring like members which are mounted on inner member 24 as described above and are preferably made of a memory alloy such as nitinol (nickel titanium). Thus, marker bands or pillow support members 30 and 32 may be distorted as, for example, during the insertion or retraction process and still spring back to their original shape. Of course, if the proximal and distal support members are not subjected to significant distortion forces, metals such as stainless steel, tungsten, and the like may be used.

It should be appreciated that marker bands 30 and 32 may be of any geometry which offers the required pillow support so as to maintain the outer diameter of the pillows equal to or greater than the outer diameter of the stent. For example, referring to FIG. 4, there is shown a tapered marker band or pillow support member 48 which has an outer diameter only slightly larger than the diameter of inner member 24 at its proximal end and tapers to a larger diameter at its distal end adjacent the edge of stent 22 so as to maintain the outer diameter of pillow 38 substantially equal to or greater than the outer diameter of stent 22. As was the case with the coiled marker bands shown in FIGS. 1, 2, and 3, marker band 48 is made of a radiopaque substance so as to be visible with low level X-rays thus assisting in the positioning of stent 22 within the target lesion.

Figure 5:
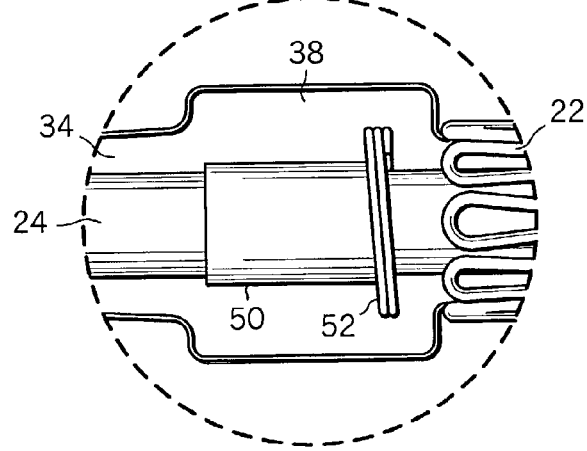
FIG. 5 is an enlarged view of a marker band and pillow support assembly in accordance with a still further embodiment of the present invention.

FIG. 5 illustrates another embodiment of the pillow support member in accordance with the teachings of the present invention. In this embodiment, a solid tubular marker band section 50 (e.g. a section of tubing having a length of, for example, one millimeter and made of platinum iridium or the like) has an outer diameter which is sufficient to permit section 50 to be positioned and retained on inner member or guide lumen 24. Another section 52 is fixedly coupled to or integrally formed with the distal end of marker band tube 50 adjacent to the proximal end of stent 22 and has an outer diameter greater than the outer diameter of section 50 so as to support pillow 38. The outer diameter of section 52 is large enough to maintain the outer diameter of pillow 38 at least equal to or greater than the outer diameter of stent 22. While support section 52 is shown as comprising a coil as was the case in the embodiment shown in FIGS. 1, 2, and 3, it should be appreciated that support section 52 may be solid or take on any other configuration which provides the necessary support to pillow 38.

Figure 6:
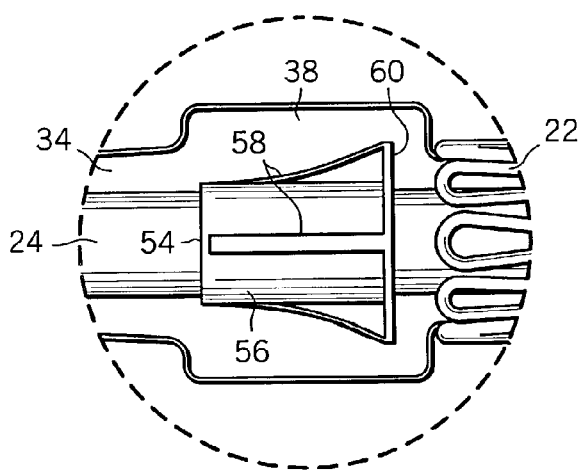
FIG. 6 is an enlarged view of a marker band and pillow support assembly in accordance with a still further embodiment of the present invention.
Figure 7:
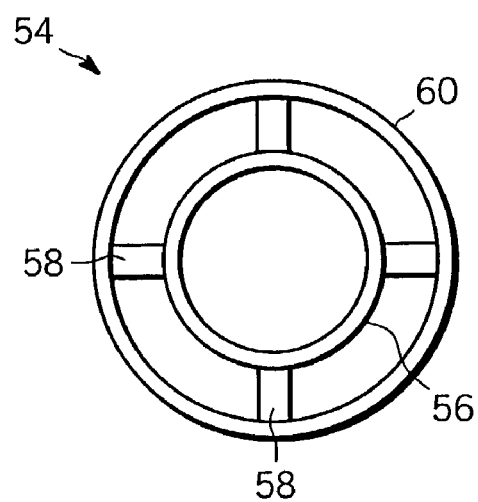
FIG. 7 is a front view of the marker band and pillow support assembly shown in FIG. 6.
Figure 8:
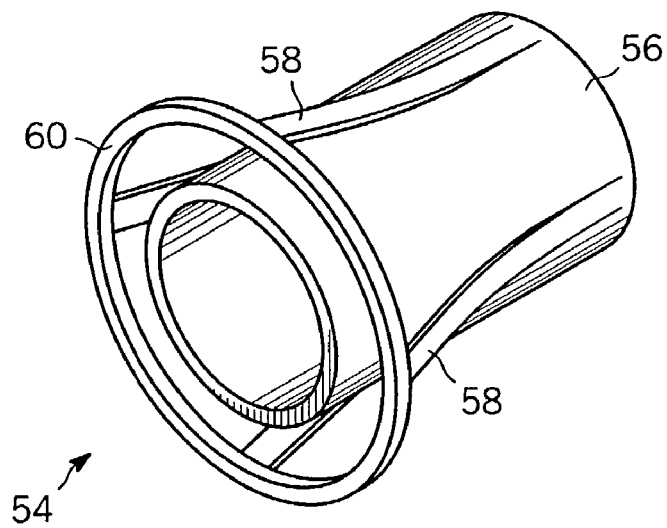
FIG. 8 is an isometric view of the marker band and pillow support assembly shown in FIG. 6.

FIG. 6 illustrates a still further embodiment of the present invention. In this case, a marker band and pillow support member shown generally at 54 includes a central tubular member 56 (e.g., of the type shown in FIG. 5) which has an outer diameter which permits it to be positioned and held on inner member or wire lumen 24. A plurality of leaf springs 58 are fixedly coupled to, as for example by brazing or welding, the proximal end of tubular member 56. Leaf spring members 58 terminate at coil or ring 60 and are fixedly coupled thereto. The marker band/pillow support member 54 in accordance with this, embodiment is shown in more detail in FIGS. 7 and 8 which are front and isometric views. Leaf springs 58 are made of a memory alloy which may be deflected or distorted and spring back to their original shape. Thus, ring 60 may float when subjected to significant distortion and still return to its original position so as to maintain the outer diameter of pillow 38 equal to or greater than the outer diameter of stent 22.

Thus, there has been provided an intravascular support device which includes radiopaque marker bands to assist in proper positioning of the device and which also support pillows 36 and 38 so as to assure a smooth transition between stent 22 and pillows 36 and 38 when the device is being inserted into a target lesion or extracted back into the guide catheter. While the primary application for the device is presently in the treatment of cardiovascular disease such as atherosclerosis or other forms of coronary narrowing, the device may also be used in the treatment of vessels elsewhere in the body such as the kidney, leg, etc. It should be clear that in such cases, the size of the stent would be adjusted to accommodate the different sizes of vessels being treated.

In the foregoing specification, the invention has been described with reference to specific embodiments. It should be appreciated, however, that various modifications and changes might be made without departing from the scope of the invention as set forth in the appended claims. Accordingly, the specification and figures should be regarded as illustrative rather than restrictive, and all such modifications are intended to be included within the scope of the present invention.

What is claimed is:

1. A stent delivery system, comprising:
   an inner member;
   an expandable balloon mounted in a collapsed state on said inner member, said expandable balloon having a first end and a second end;
   a compressible stent mounted in a compressed state around said expandable balloon between said first and second ends, said compressible stent in said compressed state having a first diameter;
   at least a first retainer pillow formed in said expandable balloon at said first end and having a first outer diameter at least substantially equal to said first diameter; and
   at least a first pillow support member mounted on said inner member for supporting said first retainer pillow to maintain said first outer diameter; said first pillow support member comprising a coiled spring member having a first section of a second diameter for engaging said inner member, and a second section of a third diameter being greater than said second diameter of said first section,for supporting said at least a first retainer pillow.

2. A stent delivery system according to claim 1 further comprising:
   at least a second retainer pillow formed in said expandable balloon at said second end and having a second outer diameter at least substantially equal to said first diameter; and
   at least a second support member mounted on said inner member for supporting said second retainer pillow to maintain said second outer diameter.

3. A stent delivery system according to claim 2 wherein said first outer diameter is greater than said first diameter.

4. A stent delivery system according to claim 1 wherein said coiled spring member is made of a memory alloy.

5. A stent delivery system according to claim 4 wherein said memory alloy is nickel-titanium.

* * * * *